United States Patent
Sucec et al.

(10) Patent No.: US 8,617,227 B2
(45) Date of Patent: Dec. 31, 2013

(54) BONE CONNECTOR WITH PIVOTABLE JOINT

(75) Inventors: Matthew C. Sucec, Portland, OR (US); Thomas C. Tuller, Surprise, AZ (US)

(73) Assignee: Acumed LLC, Hillsboro, OR (US)

( * ) Notice: Subject to any disclaimer, the term of this patent is extended or adjusted under 35 U.S.C. 154(b) by 177 days.

(21) Appl. No.: 13/115,529

(22) Filed: May 25, 2011

(65) Prior Publication Data

US 2011/0224738 A1    Sep. 15, 2011

Related U.S. Application Data

(63) Continuation of application No. 11/431,740, filed on May 9, 2006, now Pat. No. 7,951,198.

(60) Provisional application No. 60/679,710, filed on May 10, 2005, provisional application No. 60/701,891, filed on Jul. 21, 2005.

(51) Int. Cl.
*A61B 17/86* (2006.01)

(52) U.S. Cl.
USPC .............. 606/328; 606/320; 623/13.14

(58) Field of Classification Search
USPC .............. 606/53–59, 60, 246, 247, 250–278, 606/300–321, 323–325, 328
See application file for complete search history.

(56) References Cited

U.S. PATENT DOCUMENTS

| | | |
|---|---|---|
| 1,258,580 A | 3/1918 | Lassiter |
| 2,112,007 A * | 3/1938 | Adams .......................... 433/174 |
| 2,381,050 A | 8/1945 | Hardinge |
| 3,916,451 A | 11/1975 | Buechel et al. |
| 4,275,490 A | 6/1981 | Bivins |
| 4,276,660 A | 7/1981 | Laure |
| 4,640,271 A | 2/1987 | Lower |
| 4,750,492 A | 6/1988 | Jacobs |
| 4,828,562 A | 5/1989 | Kenna |
| 4,858,601 A * | 8/1989 | Glisson .......................... 606/916 |
| 4,870,957 A | 10/1989 | Goble et al. |
| 4,950,270 A | 8/1990 | Bowman et al. |
| RE33,348 E | 9/1990 | Lower |
| 4,955,910 A | 9/1990 | Bolesky |
| 4,955,916 A | 9/1990 | Carignan et al. |
| 5,108,437 A | 4/1992 | Mansat et al. |
| 5,151,104 A | 9/1992 | Kenna |
| 5,217,462 A | 6/1993 | Asnis et al. |
| 5,236,445 A | 8/1993 | Hayhurst et al. |
| 5,281,422 A | 1/1994 | Badylak et al. |

(Continued)

FOREIGN PATENT DOCUMENTS

| | | |
|---|---|---|
| GB | 2441690 B | 11/2010 |
| WO | 9834567 A1 | 8/1998 |

(Continued)

OTHER PUBLICATIONS

Japan Patent Office, Notice of Reasons for Rejection, Japanese Patent Application No. 2008-511334; mailed Jan. 31, 2012.

(Continued)

*Primary Examiner* — Pedro Philogene
*Assistant Examiner* — Lynnsy Schneider
(74) *Attorney, Agent, or Firm* — Kolisch Hartwell, P.C.

(57) ABSTRACT

System, including methods, apparatus, and kits, for connecting bones and/or bone portions using a bone connector with a pivotable joint.

20 Claims, 8 Drawing Sheets

(56) References Cited

U.S. PATENT DOCUMENTS

| | | | |
|---|---|---|---|
| 5,306,301 A | 4/1994 | Graf et al. | |
| 5,486,197 A | 1/1996 | Le et al. | |
| 5,489,210 A | 2/1996 | Hanosh | |
| 5,498,265 A | 3/1996 | Asnis et al. | |
| 5,645,588 A | 7/1997 | Graf et al. | |
| 5,665,089 A | 9/1997 | Dall et al. | |
| 5,707,395 A | 1/1998 | Li | |
| 5,741,259 A | 4/1998 | Chan | |
| 5,769,894 A | 6/1998 | Ferragamo | |
| 5,827,285 A * | 10/1998 | Bramlet | 606/60 |
| 5,868,749 A | 2/1999 | Reed | |
| 5,919,194 A | 7/1999 | Anderson | |
| 5,935,129 A | 8/1999 | McDevitt et al. | |
| 5,968,047 A | 10/1999 | Reed | |
| 5,968,078 A | 10/1999 | Grotz | |
| 5,984,924 A | 11/1999 | Asher et al. | |
| 5,993,486 A | 11/1999 | Tomatsu | |
| 6,048,344 A | 4/2000 | Schenk | |
| 6,056,752 A | 5/2000 | Roger | |
| 6,086,591 A | 7/2000 | Bojarski | |
| 6,099,530 A | 8/2000 | Simonian et al. | |
| 6,099,571 A | 8/2000 | Knapp | |
| 6,117,160 A | 9/2000 | Bonutti | |
| 6,187,008 B1 | 2/2001 | Hamman | |
| 6,250,256 B1 | 6/2001 | Lin | |
| 6,267,765 B1 | 7/2001 | Taylor et al. | |
| 6,302,886 B1 | 10/2001 | McDevitt et al. | |
| 6,319,271 B1 | 11/2001 | Schwartz et al. | |
| 6,348,053 B1 | 2/2002 | Cachia | |
| 6,368,326 B1 | 4/2002 | Dakin et al. | |
| 6,375,684 B1 | 4/2002 | Kriek | |
| 6,413,260 B1 | 7/2002 | Berrevoets et al. | |
| 6,458,134 B1 * | 10/2002 | Songer et al. | 606/304 |
| 6,471,707 B1 * | 10/2002 | Miller et al. | 606/916 |
| 6,497,726 B1 | 12/2002 | Carter et al. | |
| 6,508,830 B2 | 1/2003 | Steiner | |
| 6,517,543 B1 * | 2/2003 | Berrevoets et al. | 606/304 |
| 6,517,578 B2 | 2/2003 | Hein | |
| 6,524,314 B1 | 2/2003 | Dean et al. | |
| 6,533,802 B2 | 3/2003 | Bojarski et al. | |
| 6,562,071 B2 | 5/2003 | Jarvinen | |
| 6,575,976 B2 | 6/2003 | Grafton | |
| 6,632,224 B2 | 10/2003 | Cachia et al. | |
| 6,685,742 B1 | 2/2004 | Jackson | |
| 6,689,169 B2 | 2/2004 | Harris | |
| 6,790,208 B2 | 9/2004 | Oribe et al. | |
| 6,916,321 B2 * | 7/2005 | TenHuisen et al. | 606/312 |
| 6,918,912 B2 | 7/2005 | Seemann | |
| 6,942,666 B2 | 9/2005 | Overtaker et al. | |
| 7,367,978 B2 | 5/2008 | Drewry | |
| 7,491,236 B2 * | 2/2009 | Cragg et al. | 623/17.11 |
| 7,582,107 B2 * | 9/2009 | Trail et al. | 606/304 |
| 7,621,912 B2 * | 11/2009 | Harms et al. | 606/59 |
| 7,625,395 B2 * | 12/2009 | Muckter | 606/300 |
| 7,708,759 B2 | 5/2010 | Lubbers | |
| 7,776,068 B2 * | 8/2010 | Ainsworth et al. | 606/246 |
| 7,799,057 B2 * | 9/2010 | Hudgins et al. | 606/247 |
| 7,828,828 B2 * | 11/2010 | Lim et al. | 606/300 |
| 7,892,266 B2 * | 2/2011 | Carli | 606/301 |
| 7,951,198 B2 * | 5/2011 | Sucec et al. | 623/13.11 |
| 7,955,388 B2 * | 6/2011 | Jensen et al. | 623/13.14 |
| 7,967,850 B2 * | 6/2011 | Jackson | 606/301 |
| 8,043,334 B2 * | 10/2011 | Fisher et al. | 606/247 |
| 8,246,654 B2 * | 8/2012 | Varela | 606/247 |
| 8,292,926 B2 * | 10/2012 | Jackson | 606/257 |
| 8,308,783 B2 * | 11/2012 | Morris et al. | 606/328 |
| 2001/0051807 A1 | 12/2001 | Grafton | |
| 2002/0116013 A1 | 8/2002 | Gleason et al. | |
| 2002/0116066 A1 | 8/2002 | Chauvin et al. | |
| 2002/0161439 A1 | 10/2002 | Strobel et al. | |
| 2002/0165611 A1 | 11/2002 | Enzerick et al. | |
| 2002/0198527 A1 * | 12/2002 | Muckter | 606/73 |
| 2003/0032960 A1 | 2/2003 | Dudasik | |
| 2003/0088272 A1 | 5/2003 | Smith | |
| 2003/0153921 A1 | 8/2003 | Stewart et al. | |
| 2003/0233095 A1 | 12/2003 | Urbanski et al. | |
| 2004/0015172 A1 | 1/2004 | Biedermann et al. | |
| 2004/0068262 A1 | 4/2004 | Lemos et al. | |
| 2004/0102780 A1 * | 5/2004 | West, Jr. | 606/73 |
| 2004/0172031 A1 | 9/2004 | Rubecamp et al. | |
| 2004/0210227 A1 | 10/2004 | Trail et al. | |
| 2004/0260344 A1 | 12/2004 | Lyons et al. | |
| 2005/0113929 A1 * | 5/2005 | Cragg et al. | 623/17.16 |
| 2005/0149191 A1 | 7/2005 | Cragg | |
| 2005/0177167 A1 | 8/2005 | Muckter | |
| 2005/0245933 A1 * | 11/2005 | Sevrain | 606/73 |
| 2006/0052783 A1 | 3/2006 | Dant | |
| 2006/0079898 A1 * | 4/2006 | Ainsworth et al. | 606/61 |
| 2006/0235414 A1 | 10/2006 | Lim | |
| 2006/0264954 A1 * | 11/2006 | Sweeney et al. | 606/73 |
| 2006/0271054 A1 | 11/2006 | Sucec et al. | |
| 2007/0270813 A1 * | 11/2007 | Garamszegi | 606/61 |
| 2007/0282341 A1 * | 12/2007 | Hes et al. | 606/73 |
| 2007/0282342 A1 * | 12/2007 | Niederberger et al. | 606/73 |
| 2008/0177308 A1 * | 7/2008 | McLeer | 606/247 |
| 2008/0262556 A1 * | 10/2008 | Jacofsky et al. | 606/308 |
| 2008/0269743 A1 * | 10/2008 | McNamara et al. | 606/60 |
| 2009/0024219 A1 * | 1/2009 | McLeer | 623/17.16 |
| 2009/0062868 A1 * | 3/2009 | Casutt | 606/316 |
| 2009/0124859 A1 * | 5/2009 | Assell et al. | 600/184 |
| 2010/0280558 A1 * | 11/2010 | Biyani et al. | 606/318 |
| 2010/0331886 A1 * | 12/2010 | Fanger et al. | 606/264 |
| 2011/0004255 A1 * | 1/2011 | Weiner et al. | 606/301 |
| 2011/0040329 A1 * | 2/2011 | Ainsworth et al. | 606/246 |
| 2011/0054545 A1 * | 3/2011 | Champagne et al. | 606/301 |
| 2011/0160774 A1 * | 6/2011 | Malek | 606/255 |
| 2011/0276099 A1 * | 11/2011 | Champagne et al. | 606/328 |
| 2012/0065692 A1 * | 3/2012 | Champagne et al. | 606/311 |
| 2012/0109128 A1 * | 5/2012 | Frigg | 606/64 |
| 2012/0330364 A1 * | 12/2012 | Jacofsky et al. | 606/278 |

FOREIGN PATENT DOCUMENTS

| | | |
|---|---|---|
| WO | 2004049915 A2 | 6/2004 |
| WO | 2005092226 A1 | 10/2005 |
| WO | 2006047541 A2 | 5/2006 |

OTHER PUBLICATIONS

AcroPlate™ brochure, aap Implants, Inc., undated.
Rockwood A/C Screw (Design Rationale and Surgical Technique) brochure/flyer, DePuy Orthopaedics, Inc., 2001.
Robert, Eduardo, Authorized officer, International Preliminary Examining Authority, International Preliminary Report on Patentability, International Application No. PCT/US2006/018157, report completion date: Mar. 19, 2009; report mailing date: Jun. 9, 2009.
Stryker, UK, Medical professionals, TwinFix Cannulated compression Screw, Detailed Product Info webpage, 2006.
Young, Lee W., Authorized officer, International Searching Authority, International Search Report, International Patent Application Serial No. PCT/US2006/018157; search date: Dec. 9, 2006.
Young, Lee W., Authorized officer, International Searching Authority, Written Opinion of the International Searching Authority, International Patent Application Serial No. PCT/US2006/018157; completion date: Dec. 9, 2006.
U.K. Intellectual Property Office, Examination Report under Section 18(3), U.K. Patent Application Serial No. GB0723843.9; mailed Mar. 1, 2010.
Japan Patent Office, Notice of Reasons for Rejection, Japanese Patent application No. 2008-511334; mailed Jun. 28, 2011.
Australian Government IP Australia, Examiner's Report No. 2, Australian Patent Application Serial No. 2006244045; mailed Mar. 30, 2011.
European Patent Office, Supplementary European Search Report, European Patent Application No. EP 06759524.9; search completion date: Apr. 30, 2012; mailed May 8, 2012.
European Patent Office, Examination Report in connection with related European Patent Application No. 06 759 524.9-2310, dated Feb. 5, 2013, 4 pages.

* cited by examiner

BONE CONNECTOR WITH PIVOTABLE JOINT

CROSS-REFERENCES TO PRIORITY APPLICATIONS

This application is a continuation of U.S. patent application Ser. No. 11/431,740, filed May 9, 2006, now U.S. Pat. No. 7,951,198, which, in turn, claims the benefit under 35 U.S.C. §119(e) of the following U.S. provisional patent applications: Ser. No. 60/679,710, filed May 10, 2005; and Ser. No. 60/701,891, filed Jul. 21, 2005. Each of these priority applications is incorporated herein by reference in its entirety for all purposes.

INTRODUCTION

The skeletal portion of the human wrist, shown in FIG. 1, includes seven carpal bones 20. The carpal bones are disposed in transverse proximal 22 and distal 24 rows composed of three bones in the proximal row and four bones in the distal row. These rows provide a transition between the two bones of the forearm (radius 26 and ulna 28) and the five metacarpals 30 of the hand. The proximal row includes a scaphoid bone 32 and a lunate bone 34, among others. These bones articulate with one another (through a scapholunate joint 36), and also articulate proximally with radius 26 (through a radiocarpal joint), and distally with distal row 24 of the carpal bones.

Trauma to the wrist can produce scapholunate instability by injuring a ligament, the scapholunate interosseous ligament (SLIL) 38, that connects the scaphoid and lunate bones. The SLIL normally restricts the size of the scapholunate interval (the spacing) between the scaphoid and lunate bones and permits some limited relative rotation (about twenty degrees) of these bones about a nonfixed transverse axis extending through these bones. Injury to the SLIL can lead to arthritic degeneration of the radiocarpal joint and loss of wrist movement.

Chronic scapholunate instability may be treated with a screw, termed a Herbert screw 40. The Herbert screw extends across the scapholunate joint and threads into both the scaphoid and lunate bones using spaced threads of the screw. The Herbert screw may fix the scaphoid and lunate bones in position until engagement of the Herbert screw's thread with bone loosens enough over time to permit relative pivotal movement of the scaphoid and lunate bones about the screw's long axis. The Herbert screw thus restricts separation (i.e., relative translational motion) of the scaphoid and lunate bones both before and after pivotal movement of these bones is permitted by this screw.

The Herbert screw may have a number of disadvantages. For example, the Herbert screw may not permit bone movement for approximately six weeks after installation, a time period sufficient to result in formation of scar tissue and thus long term loss of wrist function. In addition, when the Herbert screw loosens its grip on bone, joint movement generally is restricted substantially to a pivotal motion about a single axis defined by this screw. The scapholunate joint thus cannot achieve its full anatomical range of articulation, and may be even more limited if the Herbert screw is installed at an unsuitable angle.

A number of other approaches also have been employed, alone or in combination, to treat scapholunate instability. These approaches may include percutaneous pinning, direct repair of the SLIL, dorsal capsulodesis, brunelli tenodesis, and SLIL reconstruction. However, each of these approaches may be unsatisfactory for various reasons.

SUMMARY

The present teachings provide a system, including methods, apparatus, and, kits, for connecting bones and/or bone portions using a bone connector with a pivotable joint.

DETAILED DESCRIPTION

The present teachings provide a system, including methods, apparatus, and kits, for connecting bones and/or bone portions using a bone connector with a pivotable joint ("a jointed bone connector"). The connector may include a pair of anchor elements. The anchor elements may be configured to be inserted into bone in an ordered fashion, such as a leading anchor element configured to enter bone before a trailing anchor element of the pair. In addition, each anchor element may have a retention structure that engages bone to secure the anchor element in bone. The anchor elements may be connected directly or indirectly to one another by a pivotable joint, such that separation of the anchor elements is restricted whether or not the anchor elements are engaged with bone (i.e., the anchor elements are retained proximate one another in the absence of bone). The pivotable joint may be configured to permit relative pivotal motion of the anchor elements about at least two nonparallel axes. For example, the pivotable joint may permit relative pivotal motion (1) about the long axis of the connector so that the anchor elements can be twisted relative to another, and (2) about one or more transverse axes of the connector so that the connector can be bent to place the anchor elements out of alignment. Accordingly, the shape of the connector may be flexible to accommodate, for example, (1) imperfect alignment of the connector with an anatomical axis of pivotal articulation, and/or (2) a nonfixed anatomical axis of pivotal articulation.

Figure 1:
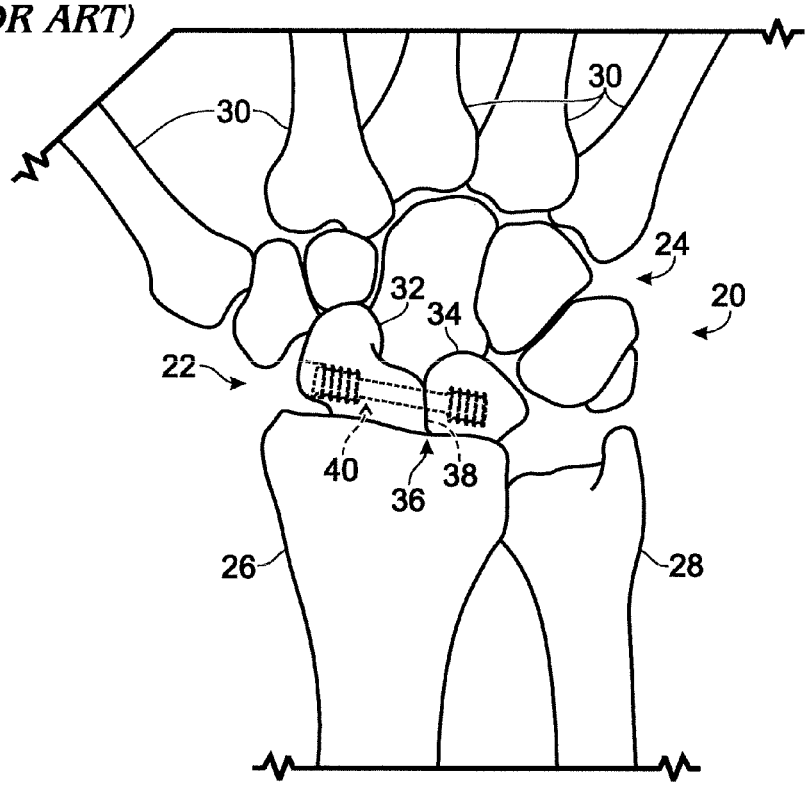
FIG. 1 is a dorsal view of the bones of the right wrist with a Herbert screw installed in and extending between the scaphoid and lunate bones.
Figure 2:
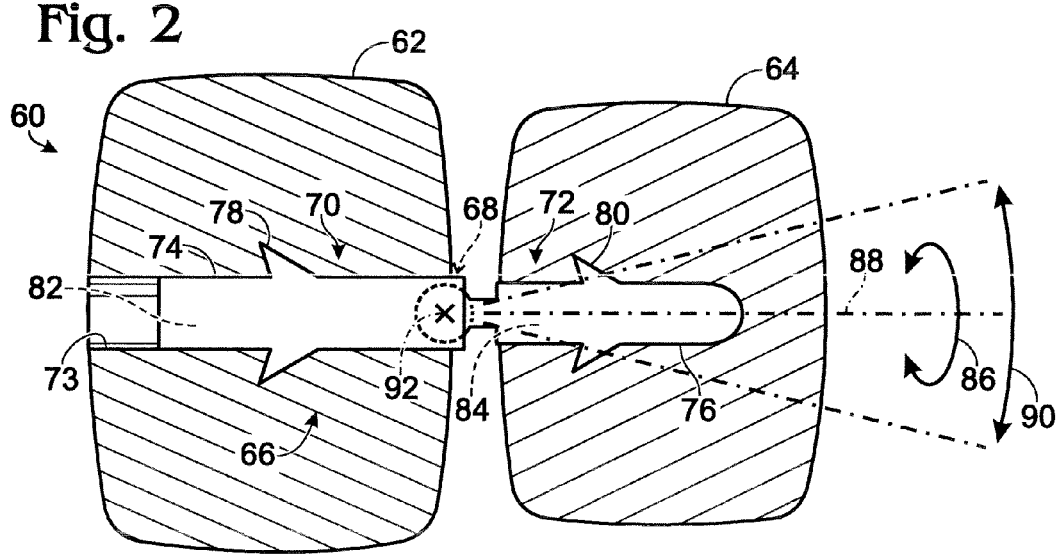
FIG. 2 is a schematic, partially sectional view of an exemplary system for connecting bone members using a bone connector with a pivotable joint, in accordance with aspects of the present teachings.

FIG. 2 shows an exemplary system 60 for connecting at least two bone members 62, 64 using a bone connector 66 with a pivotable joint 68. Bone members 62, 64 may be distinct bones or may be broken or cut fragments of the same bone.

Connector 66 may include at least a pair of anchor elements 70, 72. The connector may have a polarity provided by the anchor elements for insertion into bone (or may be configured to be inserted in either axial orientation). For example, trailing anchor element 70 may be configured to follow leading anchor element 72 into a hole 73 in proximal bone member 62 during installation of the connector. Each anchor element may have a body 74, 76 and one or more retention structures 78, 80 that engage bone to secure the anchor element in bone. The retention structures may, for example, extend laterally from the body and/or may be created by the body, such as through deformation of the body in situ (see Example 5). Accordingly, the act of placing each anchor element into bone may provide securing engagement of each retention structure with bone (such as when the connector is threaded into and/or pushed forcefully into bone), and/or at least one retention structure may be part of a retention mechanism that can be actuated selectively after placement of a corresponding anchor element into bone. Furthermore, each anchor element may have a driver engagement structure 82, 84 that allows the anchor elements to be driven into bone collectively and/or independently by a suitable driver(s).

The anchor elements may be connected to one another directly or indirectly via pivotable joint 68. The pivotable joint may permit any suitable relative pivotal motion of the anchor elements (and thus their engaged bone members), such as a twisting motion, indicated at 86, about a long axis 88 of the connector (and/or of an anchor element), and/or a bending motion, indicated at 90, about a transverse axis 92 (or a continuous range of transverse axes) defined by the joint.

Figure 3:
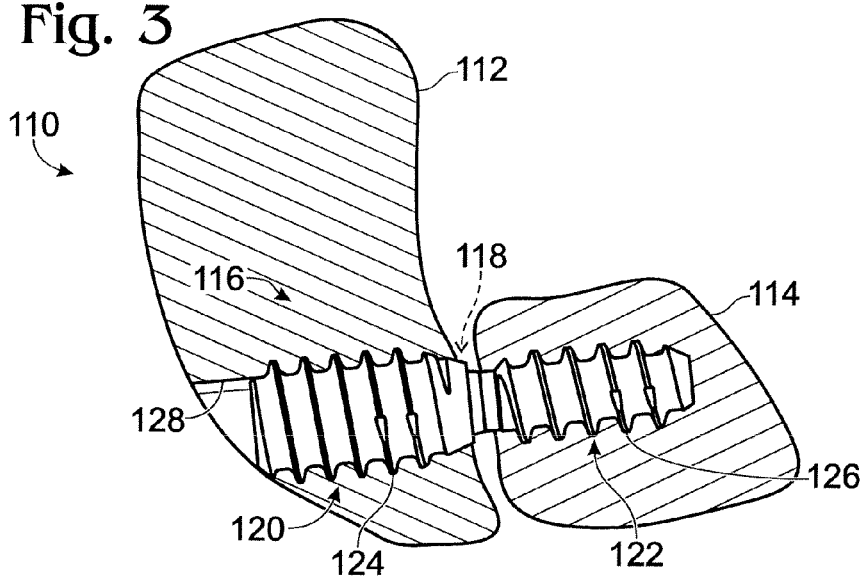
FIG. 3 is a partially sectional view of another exemplary system for connecting bone members using a bone connector with a pivotable joint, with the bone connector configured as a bone screw and connecting scaphoid and lunate bones, in accordance with aspects of the present teachings.

FIG. 3 shows an exemplary system 110 for connecting bone members, such as a scaphoid bone 112 and a lunate bone 114, using a connector configured as a bone screw 116 with a pivotable joint 118, such as a ball-and-socket joint. Bone screw 116 may include pivotably coupled screws elements 120, 122 each having an external thread 124, 126 for engagement with bone. The bone screw may be installed, for example, by forming a hole 128 in scaphoid bone 112, and placing the leading screw element into lunate bone 114 from the hole as trailing screw element 120 is advanced into the hole.

Further aspects of the present teachings are described in the following sections including (I) overview of jointed bone connectors and anchor elements, (II) retention structures, (III) pivotable joints, (IV) driver engagement structures, (V) connector compositions, (VI) fabrication of jointed bone connectors, (VII) installation of jointed bone connectors, (VIII) kits, and (IX) examples.

I. OVERVIEW OF JOINTED BONE CONNECTORS AND ANCHOR ELEMENTS

A jointed bone connector of the present teachings may include two or more components that are movable relative to one another and that have any suitable structure. The components may include two or more discrete anchor elements that can engage bone to resist removal of each anchor element. Each anchor element may be unitary (one piece) or may be formed of two or more pieces, such as two or more pieces that are affixed to one another. The jointed bone connector also may include one or more other discrete components, such as one or more discrete spacer components disposed between the anchor elements and/or one or more components flanking the anchor elements adjacent one or both opposing ends of the connector.

The anchor elements may have any suitable size and shape. The anchor elements may be about the same length (the characteristic dimension measured parallel to the central axis) or different lengths. For example, the proximal (trailing) anchor element may be shorter or longer than the distal (leading) anchor element. The anchor elements may have about the same diameter or different diameters. For example, the proximal anchor element may be wider (of greater diameter) than the distal anchor element (e.g., to ensure engagement with bone through which a narrower distal anchor element has traveled). The diameter of each anchor element may be generally constant or may vary along the length of the anchor element. For example, the distal (and/or proximal) anchor element may taper distally, proximally, or both. Furthermore, the proximal and/or distal anchor element may have a distal tapered nose (threaded or nonthreaded) that enters bone first.

The jointed bone connector may include a spacer region. The spacer region may have any suitable position(s) in the bone connector and/or within an anchor element relative to a retention mechanism of the anchor element. For example, the spacer region may be disposed between a threaded region and a joint protuberance (and/or joint cavity) of an anchor element. The spacer region may be unitary with an associated threaded region (or other retention structure) of an anchor element or may be formed by a distinct component joined fixedly (e.g., welded, bonded, or threadably coupled) or connected movably (e.g., coupled by a movable joint) to the threaded region (or other retention structure). The spacer region(s) may have any suitable length relative to the threaded region (or other retention structure) of an anchor element, including shorter, longer, or about the same length as the threaded region (or retention structure). Furthermore, the spacer region may have any suitable diameter or width relative to the threaded region (or retention structure) and/or protuberance, including a lesser (or greater) diameter or about the same diameter as that of the protuberance and/or the minor diameter of the threaded region. The spacer region may, for example, provide a nonthreaded region (and/or a non-anchoring portion of an anchor element(s)) to be disposed at the interface between bone members in which the jointed bone connector is installed and/or may help define a range of bending motion of the pivotable joint (see Section III).

The connector may define any suitable size and shape of cavity for any suitable purpose. The cavity may extend the entire length of the jointed bone connector, such that the connector is cannulated, or may, for example, terminate before or after the cavity reaches the leading anchor element and before it reaches the leading end of the jointed bone connector. The cavity may have a constant or varying cross-sectional geometry, which may be constant or vary within or compared between anchor elements. In some examples, the cavity may define a driver engagement structure in both anchor elements, so that a driver may extend through the leading anchor element and into the trailing anchor element, for concurrent engagement and rotation of both anchor elements. In some examples, the cavity may be a recess that is restricted to an actuation element disposed in the proximal anchor element (see Example 5). In some examples, the cavity may narrow (or end) as it extends distally in the leading anchor element, to provide a shoulder for a tip of the driver to bear against, to facilitate driving the connector into bone.

II. RETENTION STRUCTURES

Each anchor element may have any suitable retention mechanism. The anchor element may include a retention mechanism that is actuated by placement into bone and/or after placement into bone. The anchor elements of a jointed bone connector may have the same type of retention mechanism (e.g., each having an external thread) or may have different types of retention mechanisms (e.g., one having an external thread and another having a nonthreaded engagement with bone).

A retention mechanism that is actuated by placement into bone may be defined by an anchor element that has a cross-sectional dimension (such as diameter) that is larger than the diameter of a hole into which the anchor element is placed. The anchor element thus may be disposed in a friction fit with bone (and/or may cut into bone) as it is placed into the bone. In some examples, the cross-sectional dimension may be defined in part by one or more projections that extend laterally from the body of the anchor element. Exemplary projections may include an external thread, one or more barbs, one or more circumferential ridges, one or more hooks, and/or the like. The projections may be biased (e.g., angled toward the trailing end of the anchor element), to facilitate insertion and to restrict removal. Alternatively, or in addition, the anchor element may have a cross-sectional dimension that increases toward an end (such as a trailing end) of the anchor element (e.g., a flared (e.g., frustoconical) anchor element). Anchor elements that engage bone and resist removal as they are placed into bone may be driven into bone rotationally (e.g., threaded into bone) and/or translationally (e.g., hammered into bone).

A retention mechanism that can be actuated in situ after placement of an anchor element into bone may be provided by expansion/deformation of the anchor element at a selected time after placement. The expansion/deformation may be any change in the structure of the anchor element that increases a cross-sectional dimension of the anchor element at one or more (or all) positions along the placement axis (e.g., the long axis) of the anchor element. Further aspects of retention mechanisms actuated selectively in situ are described in Example 5.

The jointed bone connector may be configured as a bone screw having one or more anchor elements ("screw elements") with an external thread. The external thread may have any suitable thread structure. Each screw element may include a single thread (e.g., a continuous rib and/or furrow) or a plurality of threads. The plurality of threads may be disposed in discrete axial regions of the screw element (e.g., spaced proximal and distal threaded regions on the screw element) and/or may share the same axial region (e.g., to produce a multi-threaded configuration). The thread (or threaded region) of each screw element may extend over any suitable portion of the screw element's length, including at least substantially the entire length or less than about half the length, among others. The screw elements may have a thread of the same pitch or of different pitch. For example, the trailing screw element may have a thread with a lesser (or greater) pitch than a thread of the leading screw element, to facilitate compression (or distraction) of associated bone members during installation of a jointed bone screw. In addition, the pitch within each screw element may be constant or may vary, for example, decreasing (or increasing) toward the proximal end of the screw element. The thread may have any other suitable features. For example, the thread (and thus the corresponding screw element) may have a constant or varying major and/or minor diameter within a screw element and/or between the screw elements.

In some embodiments of jointed bone screws, the screw elements, and particularly the leading screw element, may be configured to be self-drilling and/or self-tapping as the bone screw is advanced into bone. For example, a leading end region of the leading screw element may include a cutting structure(s) to drill bone, and/or a threaded region of either or both screw elements may include a tap region (such as one or more axial flutes and/or thread notches, among others) with a cutting edge(s) to tap bone.

III. PIVOTABLE JOINTS

The anchor elements of a jointed bone connector may be connected by any suitable joint. The joint may be a movable joint between the anchor elements, operating by relative sliding motion (pivotal and/or translational) of apposed joint constituents. The joint may operate to restrict complete separation of the anchor elements in the absence of bone, while permitting relative pivotal and/or translational motion of the anchor elements. The joint may be a single connection between the anchor elements or a composite connection formed collectively by two or more distinct movable joints.

The joint may be formed by slidable contact between the anchor elements. For example, the joint may be formed by a protuberance (e.g., a head) of one anchor element received in a cavity defined by the other anchor element. The protuberance may be provided by the trailing or leading anchor element. The protuberance may be sized and/or shaped to be received and retained in the cavity. For example, the protuberance may have a characteristic dimension (such as width or diameter) that is greater than the mouth of the cavity, such that the protuberance, after being received in the cavity, resists withdrawal through the mouth. However, in some embodiments, the characteristic dimension may be close enough to the size of the mouth that the protuberance can be forced into the cavity through the mouth. The protuberance and the cavity may have generally complementary shapes or different shapes. In some examples, the protuberance and/or the cavity may be semispherical (that is, being at least somewhat spherical in shape, to create a ball-and-socket joint), cylindrical (such as a hinge joint), conical, and/or the like. The protuberance and cavity may correspond relatively closely in size, and/or the cavity may be somewhat larger in an axial and/or transverse direction, to permit, for example, axial and/or side-to-side (lateral) motion, respectively, of the protuberance within the cavity (e.g., see Example 4).

The joint may permit any suitable relative motion. The joint may permit axial translational motion and/or lateral translational motion, or may substantially restrict either or both of these motions. The joint also or alternatively may permit pivotal motion about the long axis and/or about one or more transverse axes of the jointed bone connector. The pivotal motion about the long axis may be unrestricted (allowing a full turn) or restricted to less than a full rotation of the anchor elements. The pivotal motion about the transverse axes may be determined by the structure of the pivotable joint and/or joint constituents, for example, allowing an angular range of motion, about a selected transverse axis, of at least about five degrees and/or no more than about 10, 20, 40, or 90 degrees, among others.

IV. DRIVER ENGAGEMENT STRUCTURES

The jointed bone connector may have one or more structures for engagement with a driver, to facilitate driving the connector into bone. For example, only one of the anchor elements may have a driver engagement structure (see, e.g., Example 5), or each anchor element of the connector may have a driver engagement structure (see, e.g., Examples 1-3). The driver engagement structures of the connector may have the same cross-sectional size and shape (see, e.g., Examples 2 and 3) or may have different cross-sectional sizes or shapes (see, e.g., Example 1). Accordingly, the driver engagement structures may be engaged concurrently with the same driver, such as to rotate the anchor elements together, or at least one driver engagement structure may be engaged selectively, such as for selective rotation of an anchor element (e.g., to adjust the spacing between bone members to a greater or less spacing).

The driver engagement structure may be defined by a cavity (or cavities) or a projection(s). Exemplary cavities (i.e., through-holes, blind holes, and/or recesses) may have any suitable cross-sectional shape for use with a rotational driver, such as polygonal, cruciform, rosette, slotted, circular (with a set of two or more laterally disposed cavities), etc. In some examples, a circular cross-sectional shape may be suitable for use with a translational driver. Exemplary projections may provide an external engagement surface, such as a hexagonal head, for engagement with a driver having a complementary socket.

Further aspects of driver engagement structures and exemplary drivers are described elsewhere in the present teachings, such as in Example 6 of Section IX.

V. CONNECTOR COMPOSITIONS

The connectors may be formed of any suitable biocompatible and/or bioresorbable material(s). Exemplary biocompatible materials include (1) metals (for example, titanium or titanium alloys; alloys with cobalt and chromium (cobalt-chrome); stainless steel; etc.); (2) plastics (for example, ultra-high molecular weight polyethylene (UHMWPE), polymethylmethacrylate (PMMA), polytetrafluoroethylene (PTFE), polyetheretherketone (PEEK), and/or PMMA/polyhydroxyethylmethacrylate (PHEMA)); (3) ceramics (for example, alumina, beryllia, calcium phosphate, and/or zirconia, among others); (4) composites; (5) bioresorbable (bioabsorbable) materials or polymers (for example, polymers of a-hydroxy carboxylic acids (e.g., polylactic acid (such as PLLA, PDLLA, and/or PDLA), polyglycolic acid, lactide/glycolide copolymers, etc.), polydioxanones, polycaprolactones, polytrimethylene carbonate, polyethylene oxide, poly-β-hydroxybutyrate, poly-β-hydroxypropionate, poly-δ-valerolactone, poly(hydroxyalkanoate)s of the PHB-PHV class, other bioresorbable polyesters, and/or natural polymers (such as collagen or other polypeptides, polysaccharides (e.g., starch, cellulose, and/or chitosan), any copolymers thereof, etc.); (6) bone tissue (e.g., bone powder and/or bone fragments); and/or the like. In some examples, these materials may form the body of an anchor element and/or a coating thereon. The anchor elements of a connector may be formed of the same material(s) or different materials. Exemplary configurations with different materials may include a connector formed of metal with trailing anchor element formed of a titanium alloy and a leading anchor element formed of cobalt-chrome (or vice versa), or a connector with a trailing anchor element formed of metal and a leading anchor element formed of a bioresorbable material or of plastic (or vice versa), among others.

VI. FABRICATION OF JOINTED BONE CONNECTORS

The jointed bone connectors of the present teachings may be fabricated by any suitable process(es). For example, the anchor elements of each jointed bone connector may be formed separately and then connected to one another. Alternatively, the anchor elements may be formed at least partially after they have been connected.

Each anchor element may be formed by any suitable process(es). Exemplary processes include molding, machining, casting, forming, crimping, milling, and/or the like. Threads or other retention structure on the anchor elements may be formed at the same time as and/or after formation of other portions of the anchor elements.

The anchor elements may be connected by any suitable process. Exemplary processes include press-fitting a protuberance of one anchor element in a cavity of another anchor element, to form a pivotable joint. The cavity may have a mouth that is narrower than the width of the protuberance, so that the protuberance, once it is forced past the mouth, remains trapped in the cavity. Other exemplary processes include disposing a protuberance in a cavity having a lip, and then crimping or otherwise deforming the lip so that the protuberance is retained in the cavity. Additional exemplary processes include placing a protuberance of a first anchor element in a cavity of a second anchor element, and then attaching a cap or other retainer to the second anchor element over the projection, such as by welding, bonding, with an adhesive, etc.

VII. INSTALLATION OF JOINTED BONE CONNECTORS

The jointed bone connectors of the present teachings may be installed by any suitable methods. Exemplary steps that may be performed are listed below. These steps may be performed in any suitable order, in any suitable combination, and any suitable number of times.

At least two bone members may be selected. The bone members may correspond to different bones or distinct fragments of the same bone, among others. The bone members may be adjacent one another naturally or may be moved so that they are adjacent one another. The bone members may have sustained or be associated with any suitable injury. For example, the bone members may result from an injury to bone (such as a fracture and/or an osteotomy, among others) or may be adjacent and/or connected to injured soft/connective tissue (e.g., ligament, tendon, and/or muscle, among others). In some examples, the bone members may be bones that articulate with one another through an anatomical joint. Any suitable anatomical joints may be selected, including the scapholunate joint, the acromioclavicular joint, etc. Any suitable adjacent bones may be selected, including bones of the hand, wrist (e.g., carpal bones), arm, foot, ankle, leg, shoulder, etc.

A jointed bone connector may be selected. The jointed bone connector may have any combination of the features described elsewhere in the present teachings. Furthermore, the jointed bone connector may have a size (e.g., length and width) selected according to the size of the bone members into which the jointed bone connector is to placed (e.g., a narrower and/or shorter jointed bone connector for smaller bone members and a wider and/or longer jointed bone connector for larger bone members).

The jointed bone connector may be placed into the bone members. In particular, a leading anchor element of the jointed bone connector may be advanced first through a more proximal (closer and/or more accessible) of the bone members and then into a more distal (farther and/or less accessible) of the bone members. A trailing anchor element of the jointed bone connector may follow the leading anchor element into the proximal bone member. The anchor elements may be positioned such that each anchor element is at least mostly (or completely) disposed within a different one of the bone members. A pivotable joint of the connector may be disposed generally between the bone members, such as overlapping with and/or proximate to an anatomical joint through which the bone members articulate. The proximity of the pivotable joint to the anatomical joint may, in some cases, at least partially determine a permitted range of transverse pivotal motion of the pivotable joint, with a smaller range permitted as the pivotable joint is positioned farther from the anatomical joint. In some examples, the jointed bone connector may include a nonthreaded region disposed between spaced threaded regions. Each threaded region may be placed at least mostly or completely in a different bone member, with the nonthreaded region extending between the bone members. In some examples, a retention mechanism may be actuated for one or both anchor elements to restrict removal of the anchor element(s) from bone, after one or both anchor elements have been placed into the bone members. In some examples, one of the anchor elements may be disposed in threaded engagement with bone during placement into bone and the other anchor element may be restricted from removal by actuation of a retention mechanism after the other anchor element is disposed in bone.

The jointed bone connector may be placed into a preformed hole in the bone members. The hole may be formed, for example, by drilling through the proximal bone member and into the distal bone member (or vice versa). In some examples, the hole may be formed by drilling over a wire placed into the bone members, to define a guide path along which a drill and the jointed bone connector travel. Accordingly, the drill and/or jointed bone connector may be cannulated so that each can slide along the wire. Alternatively, the jointed bone connector (and particularly a jointed bone screw) may be self-drilling so that it forms and/or widens its own hole as it advances into bone.

The jointed bone connector may be left in place permanently or may be removed at a later time. Removal of the jointed bone connector may take place at any suitable time. Exemplary times include at a predefined time or after a predefined amount of healing. In some examples, the jointed bone connector (and/or an anchor element thereof) may be bioresorbable, so that the jointed bone connector (and/or an anchor element thereof) is broken down by the body over time.

VIII. KITS

The jointed bone connectors of the present teachings may be provided in kits. The kits optionally may include (1) a plurality of jointed bone connectors, of the same and/or different sizes, (2) drills and/or other tools for forming holes for receiving jointed bone connectors, (3) drivers and/or other tools (such as gripping tools) for installing and/or removing jointed bone connectors from bone, (4) wires for receiving and guiding jointed bone connectors, drills, and/or drivers, as appropriate, and/or (5) a case for holding and/or organizing other components of the kit. Components of the kit may be sterile and/or sterilizable (e.g., autoclavable). In some examples, components of the kit, such as jointed bone connectors and/or wires, may be intended for single use. In some examples, components of the kit, such as drills and/or drivers, may be intended or suitable for repeated use.

IX. EXAMPLES

The following examples describe selected aspects and embodiments of systems for connecting bones and/or bone fragments using a bone connector with a pivotable joint. These examples are included for illustration and are not intended to limit or define the entire scope of the present teachings.

Example 1

Jointed Bone Screw 1

This example describes selected aspects of jointed bone screw 116; see FIGS. 4-8. Additional aspects of bone screw 116 are described above in relation to FIG. 3.

Figure 4:
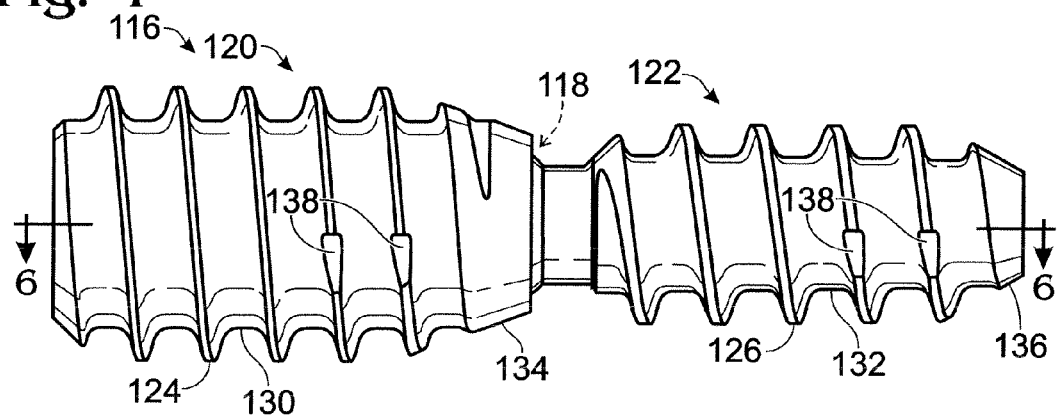
FIG. 4 is a side elevation view of the bone screw of FIG. 3 in the absence of the scaphoid and lunate bones.

FIG. 4 shows bone screw 116 in an assembled configuration with pivotable joint 118 directly connecting trailing screw element 120 to leading screw element 122. The screw elements may have any suitable size and shape. In some examples, the screw elements may have about the same diameter. Alternatively, the leading screw element may be lesser in diameter than the trailing screw element, such as having a lesser average diameter, a lesser maximum diameter, and/or a lesser median diameter than the trailing screw element. Each screw element may have a body 130, 132 on which respective external threads 124, 126 may be formed. Each body may be generally cylindrical, as shown here, and/or may taper in a linear or nonlinear fashion, such as to create a body that is partially or completely frustoconical. Furthermore, a leading region of one or both screw elements may have a tapered nose 134, 136 to, for example, facilitate centering each screw element as it enters bone.

Threads 124, 126 may have any suitable structure. For example, each thread may have one or more tap regions 138 to facilitate forming a thread in bone, generally by cutting bone. The threads may have the same pitch in each screw element or the pitches may be different. For example, as shown here, the leading screw element may have a greater (or lesser) pitch than the trailing screw element, which may tend to draw bone members together (or apart) as the bone screw is installed in bone. The tap regions may be disposed internally within each thread, as shown here, may be disposed at a leading end of the thread, and/or may be spaced from the thread, such as forward of the thread on the screw element. In some embodiments, one or more of the tap regions may structured as a notch or flute within a thread. Further aspects of thread structures that may be suitable are described elsewhere in the present teachings, such as in Section II.

Figure 5:
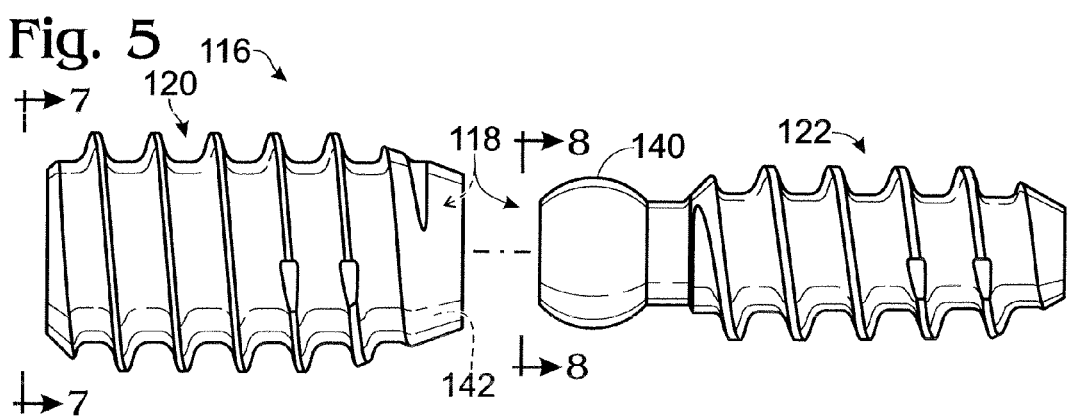
FIG. 5 is an exploded view of the bone screw of FIG. 3, taken as in FIG. 4.

FIG. 5 shows bone screw 116 with screw elements 120, 122 separated from one another. The separated configuration shown here may represent a pre-assembly configuration before the screw elements are pressed together to create pivotable joint 118. The screw elements may be assembled by placing a head (e.g., a ball) 140 of the leading (or trailing) screw element into a joint cavity or socket 142 of the trailing (or leading) screw element (see FIG. 6). After the head is received in the joint cavity, generally pressed into the joint cavity with substantial force, the ball may be trapped in the joint cavity by a wall 144 forming a mouth 146 of the cavity, to restrict separation of the screw elements (e.g., to restrict relative motion in each opposing axial direction of the bone screw). The head may be disposed adjacent a neck 147 of the screw element. The neck may be about the same diameter as the screw element body, of greater diameter, or of lesser diameter (as shown in the present illustration).

Figure 6:
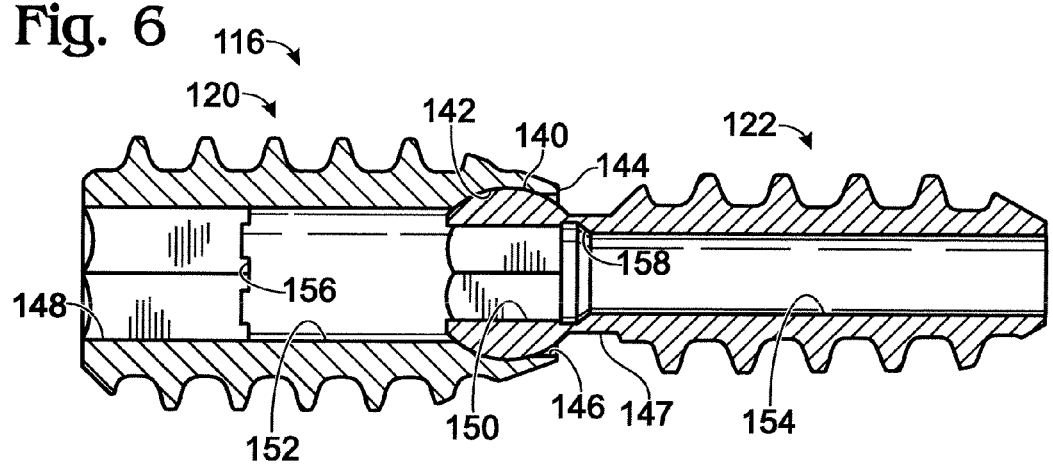
FIG. 6 is a sectional view of the bone screw of FIG. 3, taken generally along line 6-6 of FIG. 4.
Figure 7:
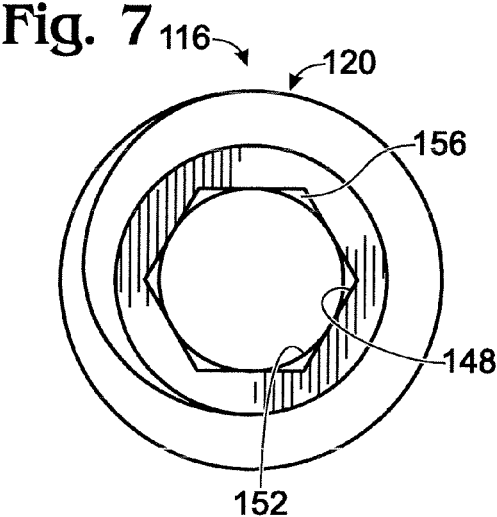
FIG. 7 is an end view of a trailing screw element of the bone screw of FIGS. 3-5, taken generally along line 7-7 of FIG. 5.
Figure 8:
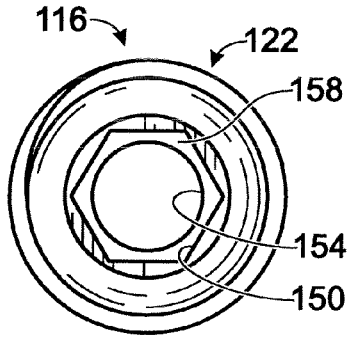
FIG. 8 is an end view of a leading screw element of the bone screw of FIGS. 3-5, taken generally along line 8-8 of FIG. 5.

FIGS. 6-8 shows additional cavities defined by the screw elements. Bone screw 116 may be cannulated, that is, hollow along its length. For example, each screw element may include a driver engagement structure 148, 150 formed as a hexagonal socket. The hexagonal sockets may be the same size or of different size, as shown here. Sockets of different size (and/or shape) may facilitate selective and/or independent engagement and rotation of each screw element with a distinct driver (or distinctly sized driver region). Each hexagonal socket may extend any suitable distance along its corresponding screw element, such as less than about one half, greater than about one half, or about the entire length. For example, in the present illustration, each hexagonal socket is disposed in a trailing region of its corresponding screw element and extends substantially less than one-half the length of the screw element. Each screw element also may have one or more additional cavities, each of lesser or greater diameter than the hexagonal socket. For example, trailing screw element 120 may have a cylindrical bore or other cavity 152 that extends from hexagonal socket 148 to joint cavity 142. Alternatively, or in addition, leading screw element 122 may have a cylindrical bore or other cavity 154 that extends from hexagonal socket 150 to the leading end of the screw element. Each bore/cavity may have a larger diameter than the hexagonal socket, to allow driver advancement past the socket, or may have a smaller diameter than the hexagonal socket, for example, to provide a forward shoulder 156, 158 against which a driver may be abutted, to restrict driver advancement and thus to position the driver axially.

Example 2

Jointed Bone Screw 2

Figure 9:
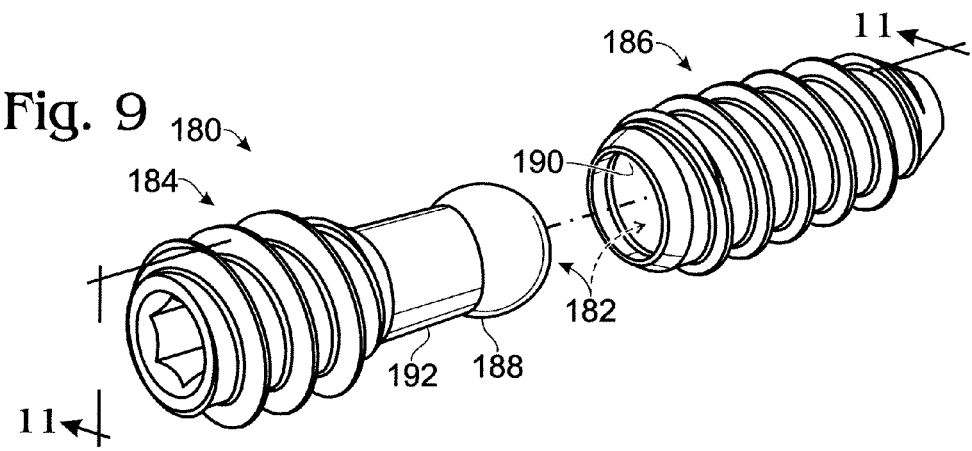
FIG. 9 is an exploded view of another exemplary bone screw with a pivotable joint, in accordance with aspects of the present teachings.
Figure 10:
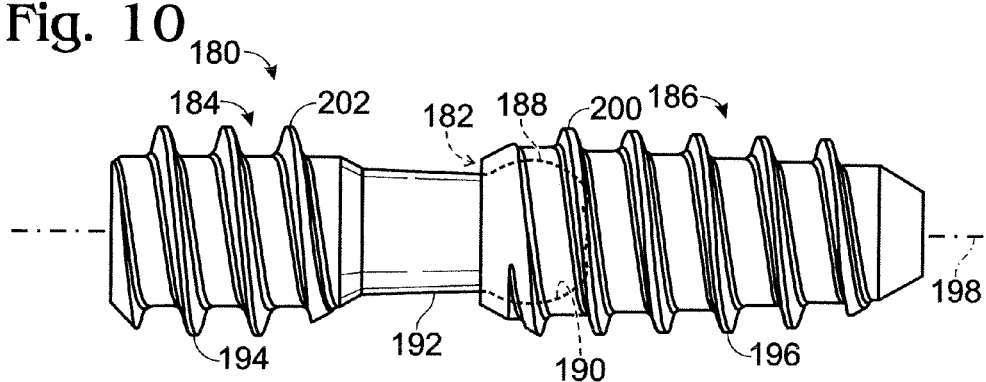
FIG. 10 is a side elevation view of the bone screw of FIG. 9 in an assembled configuration.
Figure 11:
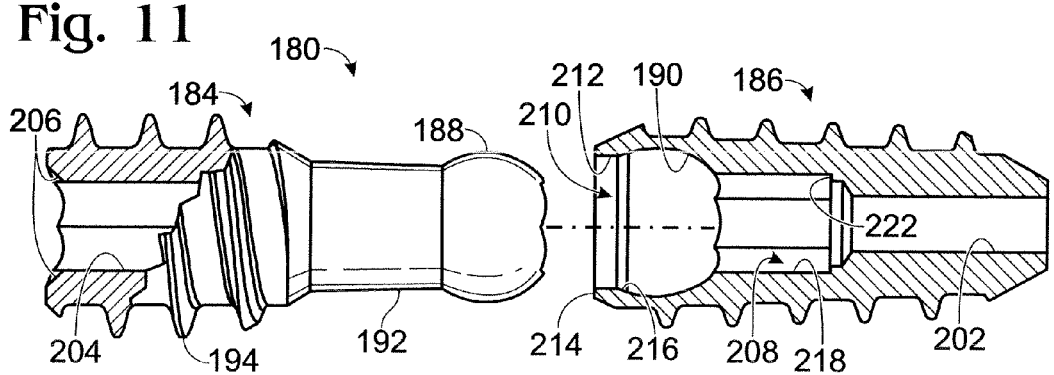
FIG. 11 is a partially sectional view of the bone screw of FIG. 9, taken generally along line 11-11 of FIG. 9.

This example describes another exemplary bone screw with a pivotable joint; see FIGS. 9-11.

FIGS. 9-11 show respective exploded, assembled, and sectional views of an exemplary bone screw 180 with a pivotable joint 182 that directly connects screw elements 184, 186. The pivotable joint of the bone screw may be formed by a protruding portion 188, such as a widened end region or head, of one of the screw elements received in a joint cavity 190 of the other screw element. The protruding portion and the joint cavity may have any suitable shapes that permit mating and relative pivotal motion. In the present illustration, the trailing screw element 184 has a semispherical head and the leading screw element defines a complementary semispherical socket disposed near the trailing end of the screw element. One or both screw elements may include a spacer or neck region 192. The spacer region may be nonthreaded and configured to space the head (or socket) from a thread 194 (or 196) (or any other suitable retention mechanism) of the trailing screw element (or leading screw element), thereby separating external threads 194, 196 (and/or other retention mechanisms) of screw elements 184, 186 (see FIG. 10).

FIG. 10 shows bone screw 180 in an aligned configuration. In this aligned configuration each of screw elements 184, 186 may be disposed generally concentrically about a central axis 198 of the bone screw, with respective long axes of the screw elements in a collinear configuration.

The screw elements may have any suitable thread configuration. In the present illustration, trailing thread 194 and leading thread 196 have about the same pitch, which may be constant within each screw element. However, in other embodiments, these pitches may differ within and/or between the screw elements. The trailing and leading threads may define major diameters (e.g., measured perpendicular to the central axis between generally opposing crests) and/or minor diameters (e.g., measured perpendicular to the central axis between generally opposing troughs) that are constant or that vary within each screw element. The major and/or minor diameters also may be the same or different when compared between the screw elements. In the present illustration, the trailing screw element has substantially constant major and minor diameters along its length. In addition, the leading screw element is tapered along its length toward a leading end of the screw element. In particular, the major diameter and the minor diameter gradually decrease toward the leading end. Furthermore, the greatest major diameter of the leading screw element, defined by a trailing region 200 of the leading screw element, may be about the same as (or less than) the major diameter of the trailing screw element, and particularly the major diameter defined by a leading region 202 of the trailing screw element (if the major diameter varies in the trailing screw element).

Bone screw 180 also may be disposed in a bent configuration. In particular, the central axes of the trailing and leading screw elements may be moved out of alignment so that the leading screw element is disposed at an angle to the trailing screw element. More generally, the leading screw element (and/or the trailing screw element) may move pivotably about a central axis defined by the leading screw element (or the trailing screw element). Furthermore, the leading screw element (and/or the trailing screw element) may move pivotably about a transverse axis (or axes) defined by the pivotable joint of the bone screw. This motion about one or more transverse axes, generally termed bending motion, may be through any angle permitted by the pivotable joint.

FIG. 11 shows exemplary hollow structure that may be defined by bone screw 180.

Trailing screw element may define a hollow 204 (e.g., a through-hole) extending through the screw element to each opposing end of the screw element. The cavity may have a noncircular cross-section, such as a hexagonal geometry, at one or more (or all) positions along the trailing screw element, to facilitate engagement by a driver (e.g., a hexagonal driver received in a hexagonal socket). Furthermore, a trailing end region 206 of the cavity may be beveled, to facilitate placing a driver into the cavity.

Leading screw element 186 also may define a hollow 208 (e.g., a through-hole) of varying cross-sectional geometry. A trailing region of the hollow may define a receiver structure 210 for ball structure 188. The receiver structure may include joint cavity 190 and a mouth region 212 adjoining the joint cavity. The mouth region may be defined by a lip 214 of the receiver structure. Accordingly, the mouth region may be part of a semispherical joint cavity, or may, for example, be a cylindrical extension of the semispherical joint cavity, as shown in the present illustration. In any case, the mouth region generally defines a narrowed section of the joint cavity, so that a shoulder 216 of lip 214 can capture the ball structure in the joint cavity and thus maintain coupling between the screw elements before, during, and after installation of the bone screw. An intermediate region of hollow 208 may define a driver engagement structure 218, for example, a hexagonal section of the hollow. A leading region of hollow 208 may narrow relative to the intermediate region to define a bore 220 and form a shoulder 222. The bore may be used, for example, for placement of the bone screw over a guide wire. The shoulder may function, for example, to position a driver axially along the bone screw and to provide a bearing surface against which the driver may be pushed axially, to facilitate installation of the bone screw.

Spacer region 192 of the trailing screw element may have any suitable shape and size. In some examples, the spacer region may be generally cylindrical or frustoconical, among others. Furthermore, the spacer region may have a smaller width (and/or diameter) than ball structure 188 joined distally to the spacer region. Furthermore, the spacer region may be narrower than threaded region 194, for example, having a diameter less than the minor diameter of the threaded region. In some examples, the diameter of the spacer region relative to the diameter of the ball structure may at least partially determine the maximum bending angle for the bone screw allowed by the pivotable joint.

Example 3

Jointed Bone Screw 3

Figure 12:
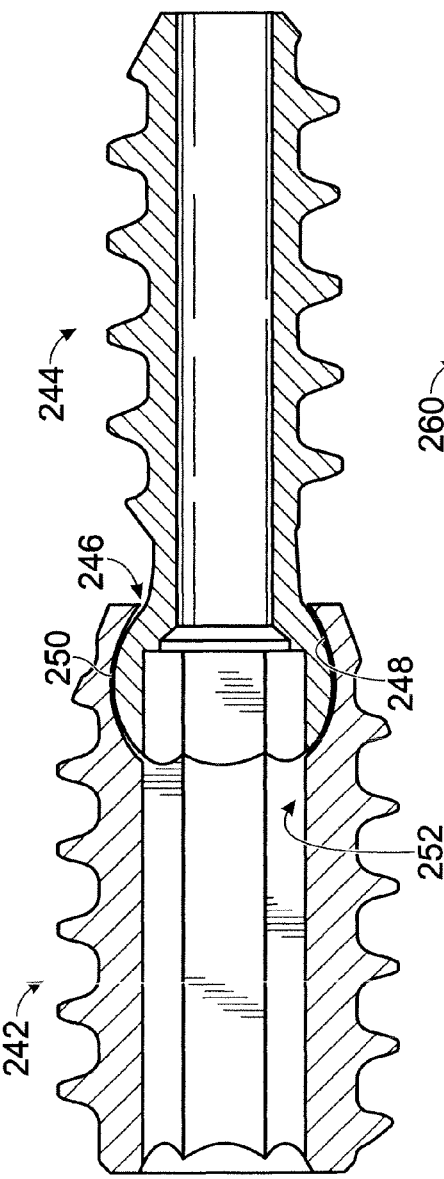
FIG. 12 is a sectional view of still another exemplary bone screw with a pivotable joint, in accordance with aspects of the present teachings.

This example describes yet another exemplary bone screw 240 with a pivotable joint; see FIG. 12.

Bone screw 240 may include a plurality of screw elements 242, 244 coupled via a ball-and-socket joint 246. A female portion or socket 248 of joint 246 may be provided by trailing screw element 242. A male portion or ball 250 of joint 246 may be provided by leading screw element 244.

The proximal and distal screw members, when aligned, cooperatively may form a driver engagement structure 252 for receiving a driver. In some embodiments, the driver engagement structure may be formed by portions forming a hole, such as a hexagonal socket, with a constant cross section. The trailing portion of the hexagonal socket may extend axially at least substantially or completely from the trailing end of the trailing screw element to joint socket 248. The leading portion of the hexagonal socket may extend any suitable distance along leading screw element 244. In some examples, the leading portion may be restricted at least substantially to ball 250 of the leading screw element. The ball may have a larger diameter than the minor diameter of the leading screw element. Accordingly, restricting the leading portion of the hexagonal socket to the ball may permit the hexagonal socket to be wider and/or the threaded region of the distal screw member to be narrower than in the jointed bone screw of Example 2.

Example 4

Jointed Bone Screw with Translational Play

Figure 13:
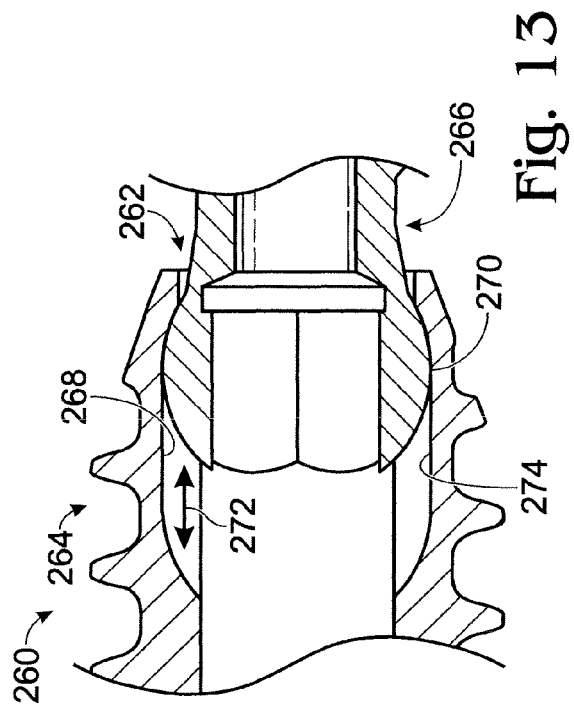
FIG. 13 is a fragmentary sectional view of yet another exemplary bone screw with a pivotable joint, in accordance with aspects of the present teachings.

This example describes an exemplary bone screw 260 with a pivotable joint that permits translational play of screw elements; see FIG. 13.

Bone screw 260 may include a pivotable joint 262 formed by a pair of screw elements 264, 266. Trailing screw element 264 may define an oblong socket 268 that receives a head 270 of the leading screw element (or vice versa). Socket 268 may be substantially larger than the head in an axial direction (oversized axially), to permit the head to slide axially, as indicated at 272 by a double-headed arrow. Accordingly, the socket may have a central region 274 that is relatively cylindrical. Alternatively, or in addition, the socket may be oversized transversely, to permit transverse play of the head within the socket. Any degree of axial and/or transverse play may be suitable, such as at least about one, two, or five millimeters.

Example 5

Jointed Bone Connector with Deformation Features

Figure 14:
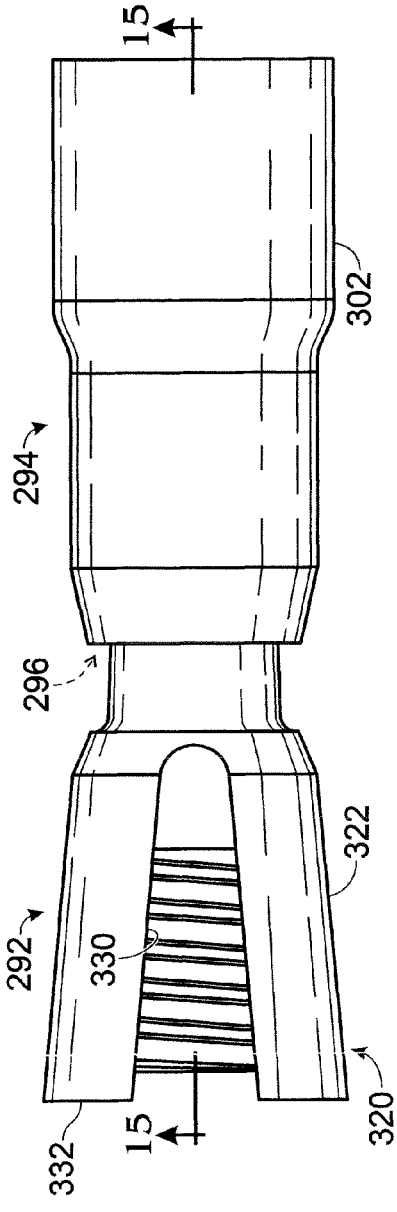
FIG. 14 is a side elevation view of an exemplary bone connector with a pivotable joint and a pair of retention mechanisms that may be actuated selectively after the bone connector is positioned in bone, in accordance with aspects of the present teachings.
Figure 15:
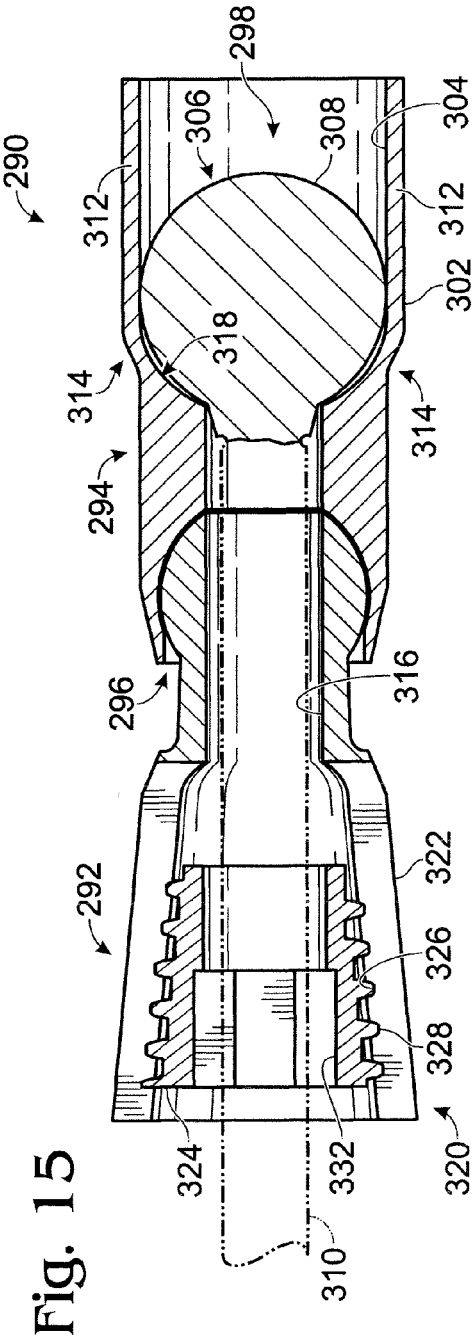
FIG. 15 is a sectional view of the bone connector of FIG. 14, taken generally along line 15-15 of FIG. 14.

This example describes an exemplary jointed bone connector 290 with deformation-based retention mechanisms that can be actuated independently and selectably with the connector disposed in bone; see FIGS. 14-15.

Jointed bone connector 290 may include a trailing anchor element 292 and a leading anchor element 294 connected by a pivotable joint 296. Each anchor element may have a cross-sectional dimension (such as a diameter) that can be increased by selective deformation of the anchor element at a suitable time, generally with the anchor element suitably disposed in bone.

The leading anchor element may be configured as a blind rivet with a nonthreaded retention mechanism 298 (see FIG. 15). The leading anchor element may include a leading body member 302 that engages bone and defines a cavity 304 configured to receive an actuation element 306 forced (e.g., pulled) into the cavity. The actuation element may be a mandrel having a head 308 and a stem or extension region 310 extending toward the trailing end of the connector from the head. The head (such as a ball) may be oversized relative to the cavity, such that walls 312 of the cavity are deformed outward, shown at 314, as the head moves into (or within) the cavity (leftward in the present illustration). The stem of the actuation element may extend through an axial bore 316 of the trailing anchor element and out of the trailing end of the trailing anchor element, so that the stem is accessible to a gripping tool. In particular, the stem may be gripped by the tool and then pulled away from the connector, to force the head of the actuation element into the cavity. The cavity may narrow (and/or taper) toward the trailing anchor element, shown at 318, to restrict further movement of the head. Accordingly, the stem of the actuation element may be configured to be detachable (e.g., broken off) after the leading retention mechanism has been actuated. (The stem of the actuator element is shown in phantom outline here to indicate its removal after detachment.) The process of actuation may anchor the leading anchor element in a distal bone member by engagement of leading body member 302 with bone.

The proximal anchor element may be retained in bone by actuation of a trailing retention mechanism 320. The trailing anchor element may include a trailing body member 322 that engages bone and a trailing actuation element 324 threadably coupled (or capable of being coupled) to the trailing body member (see FIG. 15). In particular, the trailing body member may have an internal thread 326 that engages an external thread 328 of the trailing actuation element. The trailing actuation element (and/or the external and/or internal thread) may taper toward the leading end of the connector so that threaded advancement of the actuation element into the trailing body member exerts a lateral (expansion) force on the trailing body member. The wall of the trailing body member may define axial openings 330 and intervening wall segments 332 (see FIG. 14). The wall segments may be bent outward as the actuation element is advanced rotationally (for example, with a driver disposed in recess 332 (see FIG. 15), to engage bone and thus retain the trailing anchor element in a proximal bone member.

Example 6

Exemplary Drivers

Figure 16:
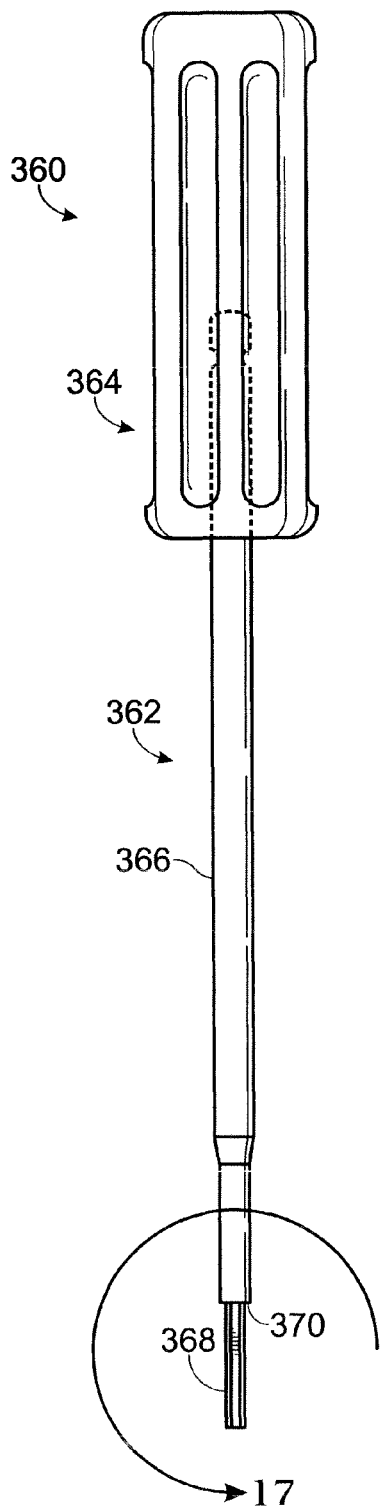
FIG. 16 is a side elevation view of an exemplary driver for installation of jointed bone connectors, in accordance with aspects of the present teachings.
Figure 17:
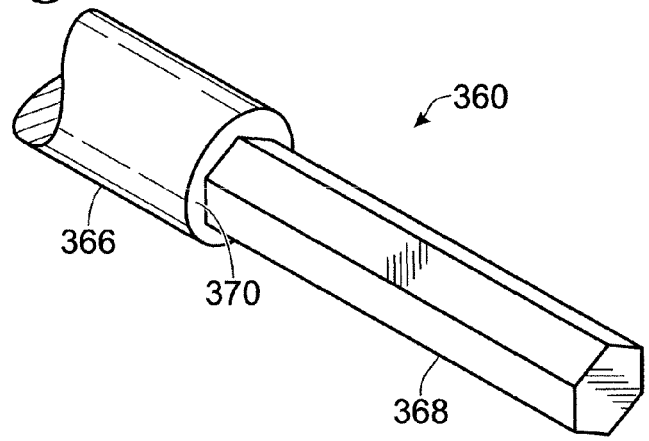
FIG. 17 is a fragmentary isometric view of the driver of FIG. 16, particularly showing a hexagonal tip region of the driver, taken generally at "17" in FIG. 16.
Figure 18:
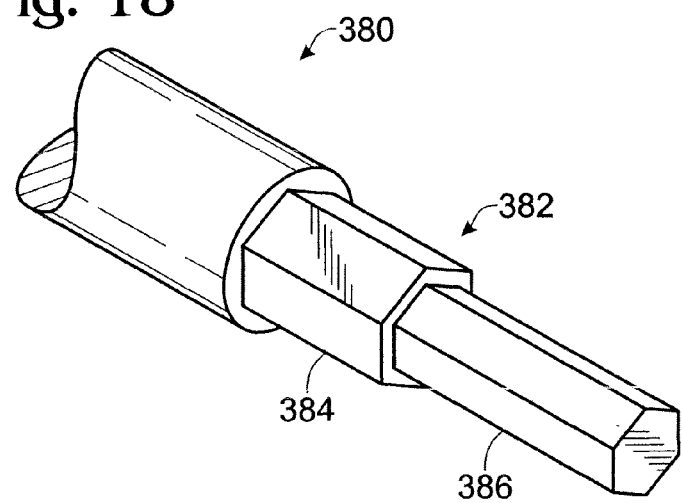
FIG. 18 is a fragmentary isometric view of another exemplary driver for installation of jointed bone connectors, particularly showing a stepped hexagonal tip region of the driver, in accordance with aspects of the present teachings.

This example describes exemplary drivers that may be suitable for installation of jointed bone connectors; see FIGS. 16-18.

FIGS. 16 and 17 show an exemplary driver 360 suitable for rotationally driving jointed bone screws into bone. Driver 360 may include a shaft 362 coupled fixedly or removably to a handle 364. The shaft may include an extension region 366 joined to a hexagonal tip region 368. The handle may be configured to be gripped by hand and may be substantially greater in diameter than the shaft, to generate more torque when turned by hand.

The hexagonal tip region may be configured to be complementary to, received in, and to engage a hexagonal socket in a jointed bone screw, such as the socket described in Example 2 (see FIG. 11) and Example 3 (see FIG. 12). Accordingly, the tip region may be sized according to the diameter and length of the hexagonal socket. In some embodiments, the tip region may be shorter than the socket. For example, a shoulder 370 formed at the distal end of extension region 366 may bear against the proximal end of the jointed bone screw when the hexagonal tip region is fully received in the hexagonal socket of the bone screw, to promote exerting an axial force on the bone screw. Alternatively, the tip region may be longer than the hexagonal socket, such that the distal end of the tip region bears against a shoulder formed in the bone screw (such as shoulder 222 of FIG. 11).

FIG. 18 shows another exemplary driver 380 for jointed bone connectors. Driver 380 may include a hexagonal tip region 382 with a stepped configuration to create hexagonal engagement regions 384, 386 of different cross-sectional sizes (i.e., different diameters). In particular, proximal engagement region 384 may be configured to be received in and to engage a hexagonal socket of larger diameter and distal engagement region 386 may be configured to be received in and to engage a hexagonal socket of smaller diameter. An exemplary jointed bone screw that may be suitable for use with driver 380 is described in Example 1 (see FIG. 6).

Drivers may be used in any suitable manner to engage and turn screw elements of a jointed bone screw. For example, both the leading and trailing screw elements of a screw may be engaged and turned at the same time, to thread the screw elements as a unit into bone. Alternatively, either a leading or a trailing screw element may be engaged and turned selectively with a suitable driver, to selectively move only one of the screw elements in relation to its engaged bone member. Accordingly, selective forward or reverse movement of only one of the screw elements may allow adjustment of the spacing between engaged bone members. For example, selective forward advancement (or reverse movement) of the leading screw element may decrease (or increase) the spacing between bone members. Furthermore, selective forward advancement (or reverse movement) of the trailing screw element may increase (or decrease) the spacing between bone members. Selectively driving only one of the screw elements of a bone screw may be performed by driver placement (e.g., by advancing the driver partially into only the more proximal region of a hexagonal socket for selective engagement only with the trailing screw element). Alternatively, or in addition, selective driving may be performed by the choice of driver structure, for example, by selecting a driver with a shorter tip region (so that the driver does not extend to the leading screw element) and/or by selecting a driver with a tip region of smaller diameter (so that the tip region cannot engage a wider socket in the trailing screw element).

Example 7

Bone Screw with Cylindrical Joint

Figure 19:
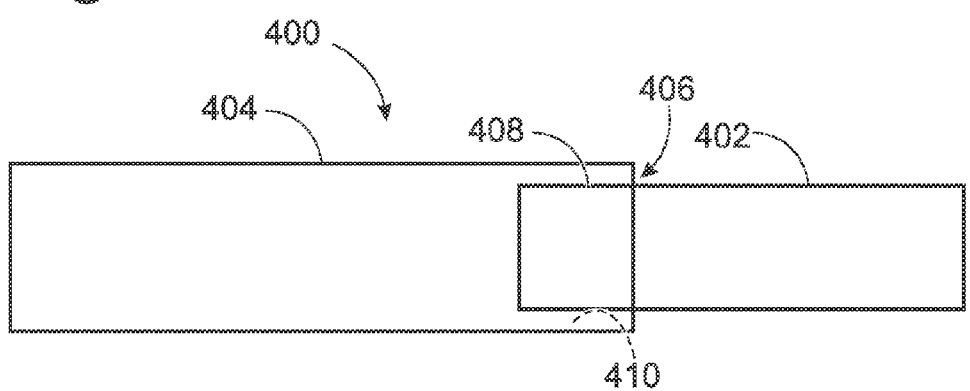
FIG. 19 is a schematic representation of an exemplary bone screw having a cylindrical joint.

FIG. 19 shows a schematic representation of an exemplary bone screw 400. The screw includes a leading screw element 402 and a trailing screw element 404 connected by a pivotable joint 406. The joint is formed by a cylindrical protuberance 408 of leading screw element 402 trapped in a cylindrical cavity 410 of trailing screw element 404.

Example 8

Selected Embodiments

This example describes selected aspects and embodiments of the present teachings, presented as a series of indexed paragraphs.

1. A device for connection of at least two bone members, comprising: (A) a proximal anchor element configured to be anchored in a proximal bone member; and (B) a distal anchor element configured to be anchored in a distal bone member, wherein the proximal and distal anchor elements define a cavity and a projection received in the cavity to form a pivotable joint that connects the proximal and distal anchor elements and allows relative bending motion of the anchor elements.

2. The device of paragraph 1, wherein each of the proximal and distal anchor elements includes an external thread for engagement with bone.

3. The device of paragraph 1, wherein at least one of the proximal and distal anchor elements includes a retention mechanism that can be actuated to anchor the at least one anchor element in a bone at a selectable time after the at least one anchor element is disposed in bone.

4. The device of paragraph 3, wherein actuation of the retention mechanism deforms the at least one anchor element.

5. The device of paragraph 4, wherein the at least one anchor element includes a body member that engages bone and an actuation element that is movable within the body member to deform the body member.

6. The device of paragraph 5, wherein the actuation element includes an external thread, and wherein the retention mechanism can be actuated by turning the actuation element.

7. The device of paragraph 5, wherein the actuation element includes an extension region that extends proximally from the at least one anchor element, and wherein the extension region is configured to be pulled proximally to deform the at least one anchor element.

8. The device of paragraph 7, wherein at least a portion of the extension region is configured to break off from the actuation element after the at least one anchor element has been deformed by pulling the actuation element.

9. The device of paragraph 3, wherein the at least one proximal and distal anchor element includes each of the proximal and distal anchor elements.

10. The device of paragraph 3, wherein only one of the proximal and distal anchor elements includes the retention mechanism, and wherein the other of the proximal and distal anchor elements includes an external thread configured to engage bone.

11. The device of paragraph 1, wherein at least one of the proximal and distal anchor elements is configured to engage bone sufficiently for anchorage during placement into the bone.

12. The device of paragraph 11, wherein the at least one anchor element is configured to be anchored in bone by driving the at least one anchor element translationally into the bone.

13. The device of paragraph 11, wherein the at least one anchor element is configured to be anchored in bone by driving the at least one anchor element rotationally into the bone.

14. A bone screw for connection of at least two bone members comprising: (A) a proximal anchor element having an external thread for engaging a proximal bone member; and (B) a distal anchor element having an external thread for engaging a distal bone member, wherein the proximal and distal anchor elements define a cavity and a projection received in the cavity to form a pivotable joint that connects the proximal and distal anchor elements and allows relative bending motion of the anchor elements.

15. The bone screw of paragraph 14, wherein the proximal and distal anchor elements cooperatively define a bore having a noncircular cross section and configured to receive a driver that turns the anchor elements for installation in bone.

16. The bone screw of paragraph 15, wherein the distal anchor element includes a proximal section and a distal section, and wherein the bore at least one of narrows and terminates within the distal section.

17. The bone screw of paragraph 14, wherein the proximal anchor element defines a long axis, and wherein the pivotable joint permits relative pivotal motion of the proximal and distal anchor elements about the long axis.

18. The bone screw of paragraph 17, wherein the pivotal motion about the long axis is unrestricted such that the distal anchor element can be rotated through a full turn.

19. The bone screw of paragraph 14, wherein the projection is defined by the proximal anchor element, and wherein the projection is generally spherical.

20. The bone screw of paragraph 14, wherein each of the proximal and distal anchor elements includes a thread having a pitch, and wherein the pitch is about the same for the anchor elements.

21. The bone screw of paragraph 14, wherein the distal anchor element includes a length, a distal end, and a thread defining a major diameter, and wherein the major diameter of the thread decreases gradually toward the distal end along a substantial portion of the length.

22. The bone screw of paragraph 21, wherein the major diameter of the distal anchor element has a maximum, wherein the proximal anchor element includes a thread defining a major diameter with an average, and wherein the maximum is about the same as the average.

23. The bone screw of paragraph 14, wherein each of the proximal and distal anchor elements is unitary.

24. The bone screw of paragraph 14, wherein each of the proximal and distal anchor elements includes a threaded region, and wherein at least one of the proximal and distal anchor elements includes a nonthreaded region disposed generally between the threaded regions.

25. The bone screw of paragraph 24, wherein the nonthreaded region is included in the one anchor element having the projection, and wherein the nonthreaded region is disposed generally between the projection and the threaded region of the one anchor element.

26. A kit for connection of at least two bone members, comprising: (A) a first device or bone screw according to any one of paragraphs 1-25; and (B) at least one of a second device or bone screw according to any one of paragraphs 1-25, a drill for forming a hole in bone for receiving the first device or bone screw, a driver for installing and/or removing the first device or bone screw from bone, and a wire for receiving a bone screw, driver, and/or drill.

27. A method of connecting bone members, comprising: (A) selecting a pair of adjacent bone members; (B) selecting a device or bone screw according to any one of paragraphs 1-25; and (C) installing the device or bone screw in the adjacent bone members such that each anchor element is at least substantially disposed in a different bone member.

28. The method of paragraph 27, wherein the step of selecting a pair of adjacent bone members includes selecting a scaphoid bone and a lunate bone.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

We claim:

1. A bone screw, comprising:
a first screw element and a second screw element each including an external thread for threaded engagement with bone, the screw elements being connected by a pivotable joint that traps a cylindrical protuberance of the first screw element in a cylindrical cavity of the second screw element to block removal of the cylindrical protuberance from the cylindrical cavity,
wherein the cylindrical protuberance and the cylindrical cavity are formed by a leading end region of one of the screw elements and a trailing end region of the other screw element, and
wherein the cylindrical protuberance is movable in the cylindrical cavity to permit (a) the screw elements to be twisted relative to one another about a longitudinal axis defined by one of the screw elements and (b) the bone screw to be bent about a transverse axis of the bone screw and to an angle of at least about 5 degrees from a coaxial arrangement of the screw elements.

2. The bone screw of claim 1, wherein the cylindrical cavity includes a tapered region that blocks removal of the cylindrical protuberance from the cylindrical cavity.

3. The bone screw of claim 1, wherein the cylindrical cavity includes a mouth that is narrower than a diameter of the cylindrical protuberance such that withdrawal of the protuberance from the cylindrical cavity is resisted.

4. The bone screw of claim 1, wherein the pivotable joint permits the bone screw to be bent to an angle of about 5 to 40 degrees.

5. The bone screw of claim 4, wherein the pivotable joint permits the bone screw to be bent to an angle of about 5 to 20 degrees.

6. The bone screw of claim 1, wherein the screw elements are a leading screw element and a trailing screw element, wherein the trailing screw element defines a central channel extending longitudinally through the trailing screw element, and wherein the leading screw element includes a driver engagement structure that is accessible to mate with a corresponding driver advanced to the driver engagement structure via the central channel.

7. The bone screw of claim 6, wherein the cylindrical protuberance is provided by the trailing screw element and forms a portion of the central channel.

8. The bone screw of claim 6, wherein the cylindrical protuberance is formed by the leading screw element and defines an opening that communicates with the central channel.

9. The bone screw of claim 6, wherein the external thread of the leading screw element has a larger pitch than the external thread of the trailing screw element, thereby providing compression when the screw elements are driven into bone.

10. The bone screw of claim 6, wherein the leading screw element is smaller in diameter on average than the trailing screw element.

11. The bone screw of claim 1, wherein each of the screw elements is only one discrete piece.

12. The bone screw of claim 1, wherein the screw elements are movable relative to one another via axial motion of the cylindrical protuberance in the cylindrical cavity.

13. A method of connecting bones with a pair of screw elements connected by a pivotable joint that traps a cylindrical protuberance of one of the screw elements in a cylindrical cavity of the other screw element to block removal of the cylindrical protuberance from the cylindrical cavity, with the cylindrical protuberance and the cylindrical cavity being formed by a leading end region of a first of the screw elements and a trailing end region of a second of the screw elements, the cylindrical protuberance being movable in the cylindrical cavity to permit (a) the screw elements to be twisted relative to one another about a longitudinal axis defined by one of the screw elements and (b) the bone screw to be bent about a transverse axis of the bone screw and to an angle of at least about 5 degrees from a coaxial arrangement of the screw elements, the method comprising:

driving the bone screw into a pair of bones such that an external thread of each screw element is disposed in threaded engagement with a different bone.

14. The method of claim 13, wherein the pair of bones are a scaphoid bone and a lunate bone.

15. The method of claim 13, wherein the cylindrical cavity includes a tapered region that blocks removal of the cylindrical protuberance from the cylindrical cavity.

16. The method of claim 13, wherein the pivotable joint permits the bone screw to be bent to an angle of about 5 to 40 degrees.

17. The method of claim 13, wherein the screw elements are a leading screw element and a trailing screw element, wherein the trailing screw element defines a central channel extending longitudinally through the trailing screw element, and wherein the leading screw element includes a driver engagement structure that is accessible to mate with a corresponding driver advanced to the driver engagement structure via the central channel.

18. The method of claim 17, wherein the cylindrical protuberance is provided by the trailing screw element and forms a portion of the central channel.

19. The method of claim 17, wherein the cylindrical protuberance is formed by the leading screw element and defines an opening that communicates with the central channel.

20. The method of claim 17, wherein the external thread of the leading screw element has a larger pitch than the external thread of the trailing screw element, thereby providing compression when the bone screw is driven into the pair of bones.

* * * * *